United States Patent
Gerlach et al.

(10) Patent No.: US 7,053,246 B2
(45) Date of Patent: May 30, 2006

(54) PREPARATION OF A SYMMETRICAL SECONDARY AMINE

(75) Inventors: Till Gerlach, Ludwigshafen (DE); Frank Funke, Ludwigshafen (DE); Christoph Benisch, Mannheim (DE); Johann-Peter Melder, Böhl-Iggelheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 126 days.

(21) Appl. No.: 10/731,095

(22) Filed: Dec. 10, 2003

(65) Prior Publication Data

US 2004/0220428 A1    Nov. 4, 2004

(30) Foreign Application Priority Data

Dec. 20, 2002   (DE) ................................ 102 61 195

(51) Int. Cl.
*C07C 29/04*   (2006.01)

(52) U.S. Cl. ..................... 564/395; 564/469; 564/470; 564/486

(58) Field of Classification Search ................ 564/395, 564/469, 470, 486
See application file for complete search history.

(56) References Cited

U.S. PATENT DOCUMENTS

| | | | |
|---|---|---|---|
| 4,914,241 A | * | 4/1990 | Hesse et al. ................. 564/485 |
| 5,166,442 A | | 11/1992 | Hartwell et al. |
| 5,243,078 A | | 9/1993 | Agrawal et al. |
| 5,288,909 A | | 2/1994 | Hartwell et al. |
| 5,530,127 A | | 6/1996 | Reif et al. |
| 5,554,793 A | | 9/1996 | Hartwell et al. |
| 6,034,029 A | | 3/2000 | Wulff-Doering et al. |
| 2003/0013873 A1 | | 1/2003 | Neumann et al. |

FOREIGN PATENT DOCUMENTS

| | | |
|---|---|---|
| DE | 30 48 832 | 9/1981 |
| EP | 412 613 | 2/1991 |
| EP | 696 572 | 2/1996 |
| EP | 849 224 | 6/1998 |
| EP | 1 270 543 | 1/2003 |

OTHER PUBLICATIONS

Derwent Abst. DE 3048-832, (1981).

* cited by examiner

*Primary Examiner*—Brian J. Davis
(74) *Attorney, Agent, or Firm*—Novak, Druce & Quigg, LLP

(57) ABSTRACT

Process for preparing a symmetrical secondary amine by reaction of a primary amine in the presence of hydrogen and a catalyst whose preparation has involved precipitation of catalytically active components onto monoclinic, tetragonal or cubic zirconium dioxide.

16 Claims, 1 Drawing Sheet

PREPARATION OF A SYMMETRICAL SECONDARY AMINE

Figure 1:
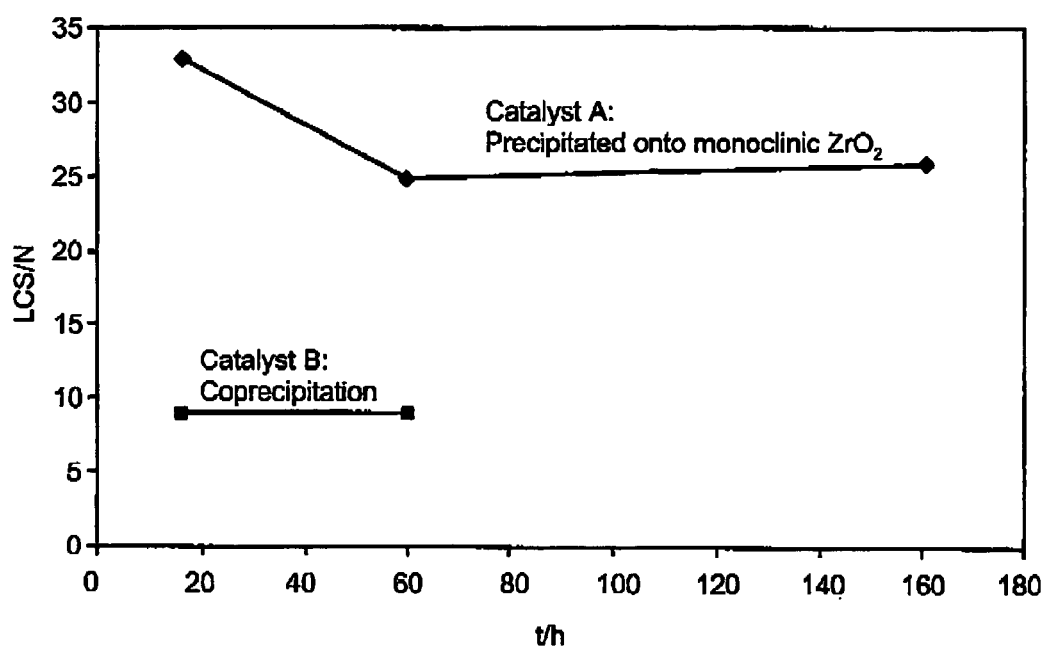

The present invention relates to a process for preparing a symmetrical secondary amine (R—NH—R; "symmetrical" indicates that the two radicals R are identical) by reaction of a primary amine (R—NH$_2$) in the presence of hydrogen and a catalyst.

Processes for preparing symmetrical secondary amines from primary amines are known per se (dimerization of the primary amine in the presence of H$_2$ with NH$_3$ formation in accordance with: 2 R—NH$_2$+H$_2$→R—NH—R+NH$_3$). Reaction of a primary amine having the desired substituents or structural elements in the presence of hydrogen under the reaction conditions selected in each case to form the desired secondary amine is prior art. A wide variety of catalysts is used here; the pressures and temperatures employed in the reaction vary greatly. A major problem in the above-described synthesis of symmetrical secondary amines is the conversion or the selectivity to the desired product, which frequently does not achieve the desired values. In addition, the use of expensive catalysts comprising noble metals is often found to be necessary.

DE-A-30 48 832 (Texaco) relates to a process for preparing bisalkylamines, in particular bis[(3-dimethylamino) propyl]amine (bis-DMAPA) from 3-(dimethylamino)propionitrile (DMAPN) or 3-(dimethylamino)propylamine (DMAPA) or mixtures of DMAPN and DMAPA. In one example, a bis-DMAPA selectivity of 80% is achieved at a DMAPA conversion of 53% at high pressure (173 bar) over Ni—Cu—Cr$_2$O$_3$; over Co—Cu—Cr$_2$O$_3$, a bis-DMAPA selectivity of 88% is achieved at a DMAPA conversion of 49%.

It is found here that, in particular, the conversions are capable of improvement. In addition, the use of chromium-free catalysts is preferred for environmental reasons.

EP-A-412 613 (Union Carbide) relates to a process for preparing amines by condensation of amino compounds such as alkylenamines in the presence of metallic phosphate catalysts.

U.S. Pat. Nos. 5,166,442, 5,288,909 and 5,554,793 (Dow) describe a reforming process for alkylenamines in the presence of group VB metal oxides, group VB metal phosphates, group IIA metal silicates and tungsten oxides.

U.S. Pat. No. 5,243,078 (Air Products) discloses a process for preparing particular polyalkylenepolyamines from linear alkylenamines in the presence of mordenite catalysts.

The earlier EP application No. 02013584.4 (BASF AG), which is not a prior publication, relates to a process for preparing particular secondary amines from primary amines in the presence of particular transition metal catalysts.

A parallel German patent application (BASF AG) filed on the same day describes a process for preparing an amine by reacting a primary or secondary alcohol, aldehyde or ketone with hydrogen and a nitrogen compound selected from the group consisting of ammonia and primary and secondary amines in the presence of a catalyst whose preparation has involved precipitation of catalytically active components onto monoclinic, tetragonal or cubic zirconium dioxide.

A parallel German patent application (BASF AG) filed on the same day relates to a process for the catalytic hydrogenation of an aliphatically unsaturated group in an organic compound using a catalyst whose preparation has involved precipitation of catalytically active components onto monoclinic, tetragonal or cubic zirconium dioxide.

A disadvantage of the heterogeneous catalyst of the prior art which comprise zirconium dioxide in the preparation of symmetrical secondary amines is, as has been recognized according to the present invention, the decrease in their mechanical stability under the reaction conditions under which they are used, in particular in the presence of reaction media comprising water. A consequence of less mechanically stable heterogeneous catalysts is a necessity of changing the catalyst in the reactor more frequently and thus a reduced space-time yield.

It is an object of the present invention to remedy the disadvantages of the prior art and to provide an improved process for preparing symmetrical secondary amines using a catalyst having improved mechanical properties under the reaction conditions of its use and thus to improve the economics of previous processes, in particular those in which catalysts comprising zirconium dioxide are used.

According to the present invention, it has been recognized that a reason for the not fully satisfactory mechanical stability, i.e. the mechanical softening, of the known catalysts comprising zirconium dioxide under reaction conditions is the fact that, for example when the abovementioned (co)precipitation technique is employed, zirconium dioxide is initially present in wholly or partially amorphous form and under the conditions of the chemical reaction catalyzed by means of these catalysts undergoes a complete or partial crystallization, i.e. conversion of the modification into tetragonal, monoclinic or cubic zirconium dioxide. In the dimerization reactions of primary amines to form symmetrical secondary amines, the reaction conditions employed usually involve an elevated temperature (e.g. 50–250° C.) and elevated pressure (e.g. 5–350 bar in the case of gas/liquid-phase reactions and gas-phase reactions).

We have found that the use of zirconium dioxide which is in a modification which is thermodynamically stable or at least metastable under the reaction conditions of the dimerization of the primary amine, e.g. monoclinic, tetragonal or cubic zirconium dioxide, in the preparation of a catalyst comprising zirconium dioxide significantly increases the mechanical stability of the resulting catalysts under the reaction conditions, particularly in the presence of reaction media comprising water.

The present invention accordingly provides a process for preparing a symmetrical secondary amine by reaction of a primary amine in the presence of hydrogen and a catalyst whose preparation has involved precipitation of catalytically active components onto monoclinic, tetragonal or cubic zirconium dioxide.

The catalytically active components precipitated on are, in particular, salts of metals selected from groups 8 to 11 (corresponding to transition groups VIII and IB) of the Periodic Table of the Elements, especially from the group consisting of Fe, Co, Ni, Ru, Rh, Pd, Pt and Cu. The metal is particularly preferably selected from the group consisting of Cu, Ni and Co.

In general, the catalysts in the process of the present invention are preferably used in the form of catalysts which consist entirely of catalytically active composition and possibly a shaping aid (e.g. graphite or stearic acid) if the catalyst is used as shaped bodies, i.e. contain no further catalytically inactive constituents.

The catalytically active composition can be introduced into the reaction vessel after milling as powder or as cross material or, preferably, introduced into the reactor after milling, mixing with shaping aids, shaping and heat treatment as shaped catalyst bodies, for example as pellets, spheres, rings, extrudates (e.g. rods).

The abovementioned concentrations (in % by weight) of the components of the catalyst are based, unless indicated otherwise, on the catalytically active composition of the catalyst prepared before treatment with hydrogen.

The catalytically active composition of the catalyst is defined as the sum of the catalytically active constituents and the composition comprises, before treatment with hydrogen, essentially the catalytically active constituents monoclinic, tetragonal or cubic zirconium dioxide (or mixtures of these modifications) and metal salts as further catalytically active components.

The sum of the abovementioned catalytically active constituents, calculated in oxidic form, e.g. as $ZrO_2$, CuO, NiO and CoO, in the catalytically active composition before treatment with hydrogen is generally from 70 to 100% by weight, preferably from 80 to 100% by weight, particularly preferably from 90 to 100% by weight, in particular from 95 to 100% by weight, very particularly preferably from >98 to 100% by weight.

The catalytically active composition of the catalysts used in the process of the present invention can further comprise one or more elements (oxidation state 0), or inorganic or organic compounds thereof, selected from groups IA to VIA and IB to VIIB and VIII of the Periodic Table.

Examples of such elements and compounds thereof are:
Transition metals such as Mn and manganese oxides, Re and rhenium oxides, Cr and chromium oxides, Mo and molybdenum oxides, W and tungsten oxides, Ta and tantalum oxides, Nb and niobium oxides or niobium oxalate, V and vanadium oxides or vanadyl pyrophosphate, zinc and zinc oxides, silver and silver oxides, lanthanides such as Ce and $CeO_2$ or Pr and $Pr_2O_3$, alkali metal oxides such as $Na_2O$, alkali metal carbonates such as $Na_2CO_3$ and $K_2CO_3$, alkaline earth metal oxides such as SrO, alkaline earth metal carbonates such as $MgCO_3$, $CaCO_3$, $BaCO_3$, phosphoric anhydrides and boron oxide ($B_2O_3$).

The catalytically active composition of preferred catalysts for use in the process of the present invention comprises, before treatment with hydrogen, from 20 to 85% by weight, preferably from 20 to 65% by weight, particularly preferably from 22 to 40% by weight, of monoclinic, tetragonal or cubic zirconium dioxide ($ZrO_2$) (or mixtures of these modifications), from 1 to 30% by weight, particularly preferably from 2 to 25% by weight, of oxygen-containing compounds of copper, calculated as CuO, and from 14 to 70% by weight, preferably from 15 to 50% by weight, particularly preferably from 21 to 45% by weight, of oxygen-containing compounds of nickel, calculated as NiO, with the molar ratio of nickel to copper preferably being greater than 1, in particular greater than 1.2, very particularly preferably from 1.8 to 8.5.

The catalytically active composition of particularly preferred catalysts further comprises, before treatment with hydrogen, from 15 to 50% by weight, particularly preferably from 21 to 45% by weight, of oxygen-containing compounds of cobalt, calculated as CoO.

The oxygen-containing compounds of copper, nickel and, if applicable, cobalt, each calculated as CuO, NiO and CoO, of the preferred catalysts are generally present in the catalytically active composition (before treatment with hydrogen) in total amounts of from 15 to 80% by weight, preferably from 35 to 80% by weight, particularly preferably from 60 to 78% by weight, with the molar ratio of nickel to copper particularly preferably being greater than 1.

The catalysts used according to the present invention can be prepared as follows.

In the preparation of the catalysts, the term "precipitation onto" refers to a procedure in which a sparingly soluble support material is suspended in a liquid, usually water, the doping components are used as readily soluble compounds and are dissolved in a liquid, usually water, and are then precipitated onto the suspended support by addition of a precipitant. (cf., for example, A. B. Stiles, Catalyst Manufacture, Marcel Dekker, Inc., 1983, p. 15).

According to the present invention, the support material used for preparation of the catalyst is zirconium dioxide in a thermodynamically stable or metastable modification, i.e. in the mono-clinic, tetragonal or cubic modification.

The basic properties of zirconium dioxide are summarized in K. Dyrek, A. Adamski, Z. Sojka, Ceramic Interfaces 2, University Press, Cambridge, 2001, pp. 241–259, including the monoclinic, tetragonal and cubic modifications which exist and their preparation.

The zirconium dioxide crystal structure can, particularly in the case of the tetragonal modification, be stabilized further by additions of one or more oxides of metals of transition group IIIB or main group IIA of the Periodic Table, in particular yttrium oxide, calcium oxide, lanthanum oxide, magnesium oxide or scandium oxide.

This stabilization effects, for example, total or partial inhibition of the conversion of the tetragonal modification into the most thermodynamically stable monoclinic modification.

To prepare the catalyst, the zirconium dioxide is suspended in a solvent, e.g. in water. The metal salts dissolved, for example, in water are then added and basic salts which are sparingly soluble or insoluble in the solvent used, e.g. water, are subsequently precipitated by addition of, for example, an alkali metal hydroxide.

The precipitates obtained in these precipitation reactions are generally not chemically uniform and usually comprise mixtures of oxides, hydrated oxides, hydroxides, carbonates and/or hydrogencarbonates of the metals used.

The precipitation can, for example, be carried out at 20–100° C., in particular 50–90° C., especially 60–80° C.

As an alternative, the metal salt solution and the alkali metal hydroxide can be introduced simultaneously into a vessel in which the zirconium dioxide support suspension is present. The support can also be suspended in the metal salt solution and this can be introduced into a precipitation vessel simultaneously with the alkali metal hydroxide.

The further catalyst preparation is then carried out by known methods, e.g. filtration, washing, drying, calcination, shaping, reduction/passivation.

The catalysts prepared in this way comprise, prior to reduction/passivation, the catalytically active metals in the form of a mixture of their oxygen-containing compounds, in particular as oxides and mixed oxides.

The catalysts can be stored as such after their preparation. Before use as catalysts for the hydrogenation of aliphatically unsaturated compounds, they are usually prereduced by treatment with hydrogen. However, they can also be used without prereduction, in which case they are then reduced under the conditions of the dimerization reaction by the hydrogen present in the reactor. To carry out the prereduction, the catalysts are generally firstly exposed to a nitrogen/hydrogen atmosphere at from 150 to 200° C. for a period of from 12 to 20 hours and subsequently treated in a hydrogen atmosphere at from 200 to 400° C. for up to about 24 hours. In this prereduction, part of the oxygen-containing metal compounds present in the catalysts is reduced to the corresponding metals, so that these are present together with the various oxygen compounds in the active form of the catalyst.

The process of the present invention is preferably used for preparing a symmetrical secondary amine of the formula I

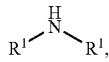
(I)

where

R$^1$ is alkyl such as C$_{1-200}$-alkyl, cycloalkyl such as C$_{3-12}$-cycloalkyl, hydroxyalkyl such as C$_{1-20}$-hydroxyalkyl, aminoalkyl such as C$_{1-20}$-aminoalkyl, hydroxyalkylaminoalkyl such as C$_{2-20}$-hydroxyalkylaminoalkyl, alkoxyalkyl such as C$_{2-30}$-alkoxyalkyl, dialkylaminoalkyl such as C$_{3-30}$-dialkylaminoalkyl, alkylaminoalkyl such as C$_{2-30}$-alkylaminoalkyl, aryl, heteroaryl, aralkyl such as C$_{7-20}$-aralkyl, heteroarylalkyl such as C$_{4-20}$-heteroarylalkyl, alkylaryl such as C$_{7-20}$-alkylaryl, alkylheteroaryl such as C$_{4-20}$-alkylheteroaryl, or R$^3$R$^4$N-A-, where A=C$_{1-6}$-alkylene or —CH$_2$—CH$_2$—O—(CH$_2$—CH$_2$—O)$_n$—CH$_2$—CH$_2$— (where n=0, 1 or 2) and R$^3$, R$^4$=C$_{1-4}$-alkyl or together with the N-atom to which they are bound form a piperidine or morpholine ring, or the two radicals R$^1$ together form —(CH$_2$)$_l$—CH$_2$—X—(CH$_2$)$_m$—, where X is CH$_2$, CHR$^5$, oxygen (O), sulfur (S) or NR$^5$, R$^5$ is hydrogen (H), alkyl such as C$_{1-4}$-alkyl, alkylphenyl such as C$_{7-40}$-alkylphenyl, l, m are each an integer from 1 to 4, by reaction of a corresponding primary amine of the formula II or IIa

(II)

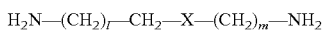
(IIa).

The substituents R$^1$, R$^3$ to R$^5$, the variable X and the indices l, m in the compounds I, II and IIa have, independently of one another, the following meanings:

R$^1$:

alkyl such as C$_{1-200}$-alkyl, preferably C$_{1-20}$-alkyl, particularly preferably C$_{1-14}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, isooctyl, 2-ethylhexyl, n-decyl, 2-n-propyl-n-heptyl, n-tridecyl, 2-n-butyl-n-nonyl and 3-n-butyl-n-nonyl, in particular C$_{1-4}$-alkyl, cycloalkyl such as C$_{3-12}$-cycloalkyl, preferably C$_{3-8}$-cycloalkyl such as cyclopropyl, cyclobutyl, cyclopentyl, cyclohexyl, cycloheptyl and cyclooctyl, particularly preferably cyclopentyl and cyclohexyl, hydroxyalkyl such as C$_{1-20}$-hydroxyalkyl, preferably C$_{1-8}$-hydroxyalkyl, particularly preferably C$_{1-4}$-hydroxyalkyl such as hydroxymethyl, 1-hydroxyethyl, 2-hydroxyethyl, 1-hydroxy-n-propyl, 2-hydroxy-n-propyl, 3-hydroxy-n-propyl and 1-(hydroxymethyl)ethyl, aminoalkyl such as C$_{1-20}$-aminoalkyl, preferably C$_{1-8}$-aminoalkyl such as aminomethyl, 2-aminoethyl, 2-amino-1,1-dimethylethyl, 2-amino-n-propyl, 3-amino-n-propyl, 4-amino-n-butyl, 5-amino-n-pentyl, N-(2-aminoethyl)-2-aminoethyl and N-(2-aminoethyl)aminomethyl, hydroxyalkylaminoalkyl such as C$_{2-20}$-hydroxyalkylaminoalkyl, preferably C$_{3-8}$-hydroxyalkylaminoalkyl such as (2-hydroxyethylamino)methyl, 2-(2-hydroxyethylamino)ethyl and 3-(2-hydroxyethylamino)propyl, alkoxyalkyl such as C$_{2-30}$-alkoxyalkyl, preferably C$_{2-20}$-alkoxyalkyl, particularly preferably C$_{2-8}$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, particularly preferably C$_{2-4}$-alkoxyalkyl, dialkylaminoalkyl such as C$_{3-30}$-dialkylaminoalkyl, preferably C$_{3-20}$-dialkylaminoalkyl, particularly preferably C$_{3-10}$-N,N-dialkylaminoalkyl such as (N,N-dimethylamino)methyl, (N,N-dibutylamino)methyl, 2-(N,N-dimethylamino)ethyl, 2-(N,N-diethylamino)ethyl, 2-(N,N-dibutylamino)ethyl, 2-(N,N-di-n-propylamino)ethyl, 2-(N,N-diisopropylamino)ethyl, (R$^5$)$_2$N—(CH$_2$)$_l$, very particularly preferably 3-(N,N-dimethylamino)propyl alkylaminoalkyl such as C$_{2-30}$-alkylaminoalkyl, preferably C$_{2-20}$-alkylaminoalkyl, particularly preferably C$_{2-8}$-alkylaminoalkyl such as methylaminomethyl, 2-(methylamino)ethyl, ethylaminomethyl, 2-(ethylamino)ethyl and 2-(isopropylamino)ethyl, (R$^5$)HN—(CH$_2$)$_q$, aryl such as phenyl, 1-naphthyl, 2-naphthyl, 1-anthryl, 2-anthryl and 9-anthryl, preferably phenyl, 1-naphthyl and 2-naphthyl, particularly preferably phenyl, heteroaryl such as 2-pyridinyl, 3-pyridinyl, 4-pyridinyl, pyrazinyl, pyrrol-3-yl, imidazol-2-yl, 2-furanyl and 3-furanyl, aralkyl such as C$_{7-20}$-aralkyl, preferably C$_{7-12}$-phenylalkyl such as benzyl, p-methoxybenzyl, 3,4-dimethoxybenzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, heteroarylalkyl such as C$_{4-20}$-heteroarylalkyl such as pyrid-2-ylmethyl, furan-2-ylmethyl, pyrrol-3-ylmethyl and imidazol-2-ylmethyl, alkylaryl such as C$_{7-20}$-alkylaryl, preferably C$_{7-12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, alkylheteroaryl such as C$_{4-20}$-alkylheteroaryl such as 2-methyl-3-pyridinyl, 4,5-dimethylimidazol-2-yl, 3-methyl-2-furanyl and 5-methyl-2-pyrazinyl, R$^3$R$^4$N-A-, where A=C$_{1-6}$-alkylene (such as —CH$_2$—CH$_2$—, —CH$_2$—CH$_2$—CH$_2$—, —CH$_2$—CH$_2$—CH$_2$—CH$_2$—) or —CH$_2$—CH$_2$—O—(CH$_2$—CH$_2$—O)$_n$—CH$_2$CH$_2$— (where n=0, 1 or 2) and R$^3$, R$^4$=C$_{1-4}$-alkyl (as defined above for R$^1$) or together with the N atom to which they are bound form a piperidine or morpholine ring, or the two radicals together form a —(CH$_2$)$_l$—CH$_2$—X—(CH$_2$)$_m$— group such as —(CH$_2$)$_4$—, —(CH$_2$)$_5$—, —(CH$_2$)$_6$—, —(CH$_2$)$_7$—, —(CH$_2$)—O—(CH$_2$)$_2$—, —(CH$_2$)—NR$^5$—(CH$_2$)$_2$—, —(CH$_2$)—CHR$^5$—(CH$_2$)$_2$—, —(CH$_2$)$_2$—O—(CH$_2$)$_2$—,
—(CH$_2$)$_2$—NR$^5$—(CH$_2$)$_2$—, —(CH$_2$)$_2$—CHR$^5$
—(CH$_2$)$_2$—, —CH$_2$—O—(CH$_2$)$_3$—, —CH$_2$—NR$^5$—(CH$_2$)$_3$—, R$^5$:
- hydrogen (H),
- alkyl, in particular C$_{1-4}$-alkyl such as methyl, ethyl, n-propyl, isopropyl, n-butyl, isobutyl, sec-butyl and tert-butyl, preferably methyl and ethyl, particularly preferably methyl,
- alkylphenyl, in particular C$_{7-40}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2-, 3-, 4-nonylphenyl, 2-, 3-, 4-decylphenyl, 2,3-, 2,4-, 2,5-, 3,4-, 3,5-dinonylphenyl, 2,3-, 2,4-, 2,5-, 3,4- and 3,5-didecylphenyl, X:
- CH$_2$, CHR$^5$, oxygen (O), sulfur (S) or NR$^5$, preferably CH$_2$, NH and O, l:
- an integer from 1 to 4 (1, 2, 3 or 4), preferably 1 and 2, m:
- an integer from 1 to 4 (1, 2, 3 or 4), preferably 1 and 2.

The primary amines which can be used in the process of the present invention can be linear, branched or cyclic. There are virtually no restrictions on the number of carbon atoms in the primary amines. The primary amines may also bear further substituents or contain functional groups which are inert under the conditions of the dimerization of symmetrical secondary amines with formation of NH$_3$, for example hydroxy, alkoxy, alkylamino or dialkylamino groups, or are also hydrogenated under the conditions of the dimerization, for example aliphatic (i.e. nonaromatic) CC double bonds and CC triple bonds.

In the process of the present invention, preference is given to using, for example, the following primary amines:
3-(dimethylamino)propylamine (DMAPA), (reaction to form bis[(3-dimethylamino)propyl]amine (bis-DMAPA),
1,3-propanediamine (reaction to form the corresponding oligomer or polymer).

The process of the present invention is generally carried out at from 50 to 250° C., preferably from 90 to 170° C., particularly preferably from 120 to 160° C., and pressures of from 5 to 350 bar, preferably from 5 to 200 bar, particularly preferably from 10 to 100 bar, in particular from 10 to 30 bar, batchwise or preferably continuously in pressure apparatuses such as autoclaves or preferably tube reactors. The pressure is preferably the hydrogen pressure in the reactor. When using a tube reactor, the catalyst used can also be present as a fixed-bed catalyst.

The reaction can be carried out in the gas phase or in the gas/liquid phase.

The space velocity over the catalyst, based on the primary amine used, is preferably from 0.1 to 2 kg l$^{-1}$h$^{-1}$, in particular from 0.8 to 1.2 kg l$^{-1}$h$^{-1}$. Part of the liquid or gaseous output from the reactor can be recirculated to the reaction.

The process of the present invention can be carried out in the absence of solvents or in solvents such as water, methanol, ethanol, tetrahydrofuran (THF), methyl tert-butyl ether (MTBE) or N-methylpyrrolidone (NMP). The primary amine used can be present as a solution in the solvent. The solvent can also be introduced separately into the reactor at any point. Preference is given to carrying out the process without use of solvents.

The desired symmetrical secondary amine obtained using the process of the present invention can be separated off from the reaction mixture and purified in a manner known per se, for example by distillation.

For example, it is possible in the work-up of the reaction product to obtain a stream comprising pure secondary amine and a stream comprising primary amine by rectification. The stream comprising the primary amine is advantageously recirculated to the synthesis.

In the process of the present invention, the (unreacted) primary amines and the symmetrical secondary amines are generally present in the crude reaction product in a weight ratio of from 10:1 to 1:10, preferably 2:3–4.

The process of the present invention advantageously makes it possible to obtain crude reaction products which contain only small amounts of tertiary amines as reaction products, generally in amounts of <10% by weight, in particular for <5% by weight, very particularly preferably from 0 to 3% by weight.

The symmetrical secondary amines obtainable by means of the process of the present invention, e.g. bis-DMAPA, can be used as hardeners for epoxy resins, catalysts for polyurethanes, intermediates for preparing quaternary ammonium compounds, plasticizers, corrosion inhibitors, textile assistants, dyes and/or emulsifiers. The symmetrical secondary amines can also be employed for producing synthetic resins, ion-exchange resins, pharmaceuticals, crop protection agents and/or pesticides.

BRIEF DESCRIPTION OF THE DRAWING(S)

FIG. 1 illustrates the lateral compressive strength of a catalyst according to the present invention and a comparative catalyst, plotted over the time of testing.

EXAMPLES

Preparation of Catalysts

Catalyst A (According to the Present Invention):

Catalyst A was prepared as follows by precipitation of the components Cu, Co and Ni onto monoclinic zirconium dioxide which has been initially placed in the precipitation vessel:

A suspension of 155 g of monoclinic zirconium dioxide powder (BET=105 m$^2$ g$^{-1}$) in 2 l of water was placed in a stirrable glass vessel and heated to 70° C. while stirring. A solution of 190.1 g of Cu(NO$_3$)$_2$×2.5 H$_2$O, 561.9 g of Ni(NO$_3$)$_2$×6 H$_2$O and 543.7 g of Co(NO$_3$)$_2$×6 H$_2$O in 2.8 l of water was then added dropwise over a period of 30 minutes. The pH was kept constant at 6.0 by simultaneous dropwise addition of a 20% strength sodium carbonate solution (700 g of Na$_2$CO$_3$ in 2.8 l of water). After addition of the solutions, the mixture was stirred at 70° C. for another 1 hour and the pH was finally increased to 7.4 by addition of sodium carbonate solution. The suspension was pumped onto a suction filter and washed with 100 l of water. The filter cake was dried at 200° C. in a drying oven for 16 hours, subsequently comminuted to a particle size of <1.6 mm and calcined at 400° C. in a stream of air (150 l/h) in a rotary tube furnace for 2 hours.

The catalyst powder obtained in this way had the composition:
28% by weight of Ni, calculated as NiO,
28% by weight of Co, calculated as CoO,
11% by weight of Cu, calculated as CuO, and
33% by weight of Zr, calculated as ZrO$_2$.

The, powder was admixed with 3% by weight of graphite, compacted, once again comminuted to <1.6 mm and finally pressed to form 4.75×3 mm pellets. The pellets were then calcined at 400° C. in air in a muffle furnace for 2 hours. The pellets were then reduced in a stream of hydrogen and nitrogen in a reduction column, firstly at 150° C. for 6 hours and then at 280° C. for 6 hours. After cooling to room temperature, the pellets were passivated in a stream of diluted air.

Catalyst B (Comparative Catalyst):

The comparative catalyst was prepared in the same way as the catalyst A according to the present invention, except that no monoclinic zirconium dioxide was initially placed in the precipitation vessel. Instead, 775 g of a zirconium acetate solution having a concentration of 20% by weight, calculated as $ZrO_2$, (based on the weight of the zirconium acetate solution) was added to the metal salt solution comprising copper, cobalt and nickel nitrates (coprecipitation). The further preparation was analogous to that of catalyst A. The catalyst powder obtained analogously had the same composition as that described for catalyst A.

Example 1

To test the mechanical stability of the catalysts A and B under the reaction conditions of the hydrogenative amination of hydroformylated polyisobutene (PIB-oxo; molar mass: 1000) the primary amine PIBA according to the reaction scheme

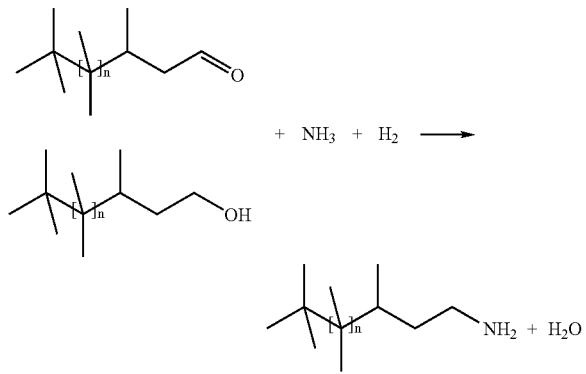

the catalysts were subjected to a boiling test in an autoclave (autoclave test) in which the reaction conditions were set as follows:

20 g of catalyst were placed in a wire basket in a stirring autoclave. 150 ml of a PIBA/Mihagol (50/50) solution were added thereto, so that the catalyst pellets were well covered with liquid. The autoclave was closed, flushed with nitrogen, the stirrer was set to a speed of 700 rpm, 50 bar of $H_2$ were injected and the contents of the autoclave were heated to 200° C. The pressure was then set to 200 bar by additional injection of $H_2$. Under these conditions, the catalyst was treated for different periods of time. The autoclave was subsequently cooled, carefully depressurized and the mechanical stability of the catalyst was determined by measuring the lateral compressive strength (LCS).

For this purpose, the catalyst pellet was subjected to an increasing force on the cylindrical surface between two parallel plates until fracture occurred. The force recorded on fracture is the lateral compressive strength. The determination was carried out on a test apparatus from Zwick, Ulm, having a fixed rotating plate and a freely movable, vertical punch which pressed the shaped body against the fixed rotating plate. The freely movable punch was connected to a load cell to measure the force. The instrument was controlled by a computer which recorded and evaluated the measured values. 25 intact pellets (i.e. pellets which were crack-free and had no broken edges) were taken from a well mixed catalyst sample, their lateral compressive strength was determined and subsequently averaged.

In the accompanying FIG. 1, the lateral compressive strengths (unit: Newton, N) of the two catalysts A and B are plotted over the time of the autoclave test (in hours).

In the case of the catalyst B prepared by coprecipitation, the X-ray diffraction pattern after the boiling test indicated that the initially X-ray amorphous $ZrO_2$ phase had be n converted into tetragonal and monoclinic $ZrO_2$. In the case of catalyst A, no recrystallization (=change of modification) was found.

Example 2

A heated tube reactor having an internal diameter of 10 mm, a centrally installed thermocouple and a total length of 35 cm is charged with 90 g of catalyst A.

Prior to the reaction, the catalyst is activated at about 180° C., firstly in a gas stream composed of nitrogen and hydrogen in a volume ratio of 4:1, subsequently in a gas stream composed of nitrogen and hydrogen in a volume ratio of 1:1 and finally in pure hydrogen.

1200 g/(l*h) of 3-(dimethylamino)propylamine (DMAPA) and 20 standard l/h (standard l=standard liters=volume at STP) of hydrogen are passed through the reactor from the bottom upward. The reactor is maintained at 140° C. and a total pressure of 30 bar.

The mixture leaving the reactor is cooled and depressurized to atmospheric pressure. The output from the reactor comprises, as main components, the desired bis[(3-dimethylamino)propyl]amine (bis-DMAPA), together with unreacted 3-(dimethylamino)propylamine (DMAPA) and small amounts of various by-products.

The liquid output from the reactor is subsequently distilled batchwise under reduced pressure and at a reflux ratio of about 5:1 in a laboratory distillation apparatus provided with random packing elements (10 theoretical plates). A fraction having a content of >97% by weight of DMAPA and a second fraction having a content of >98% by weight of bis-DMAPA are obtained.

We claim:

1. A process for preparing a symmetrical secondary amine by reaction of a primary amine in the presence of hydrogen and a catalyst whose preparation has involved precipitation of catalytically active components onto monoclinic, tetragonal or cubic zirconium dioxide.

2. A process as claimed in claim 1, wherein the catalytically active components precipitated are salts of a metal selected from transition groups VIII and IB of the Periodic Table.

3. A process as claimed in claim 1, wherein the metal salts are basic salts which are sparingly soluble or insoluble in water.

4. A process as claimed in claim 2, wherein the salts are oxides, hydrated oxides, hydroxides, carbonates and/or hydrogencarbonates.

5. A process as claimed in claim 2, wherein the metal is selected from the group consisting of Fe, Co, Ni, Ru, Rh, Pd, Pt and Cu.

6. A process as claimed in claim 2, wherein the metal is selected from the group consisting of Cu, Ni and Co.

7. A process as claimed in claim 1, wherein the catalytically active composition of the catalyst before treatment with hydrogen comprises
from 20 to 85% by weight of oxygen-containing compounds of zirconium, calculated as $ZrO_2$,
from 1 to 30% by weight of oxygen-containing compounds of copper, calculated as CuO, and
from 14 to 70% by weight of oxygen-containing compounds of nickel, calculated as NiO.

8. A process as claimed in claim 1, wherein the catalytically active composition of the catalyst before treatment with hydrogen comprises
from 20 to 65% by weight of oxygen-containing compounds of zirconium, calculated as $ZrO_2$,
from 1 to 30% by weight of oxygen-containing compounds of copper, calculated as CuO,
from 15 to 50% by weight of oxygen-containing compounds of nickel, calculated as NiO, and
from 15 to 50% by weight of oxygen-containing compounds of cobalt, calculated as CoO.

9. A process as claimed in claim 7, wherein the molar ratio of nickel to copper is greater than 1.

10. A process as claimed in claim 1, wherein the monoclinic, tetragonal or cubic zirconium dioxide contains one or more oxides of metals of transition groups IIIB or main group IIA of the Periodic Table.

11. A process as claimed in claim 1, wherein the reaction is carried out at from 50 to 250° C.

12. A process as claimed in claim 1, wherein the reaction is carried out at pressures of from 5 to 350 bar in the gas/liquid phase or in the gas phase.

13. A process as claimed in claim 1 for preparing a symmetrical secondary amine of the formula I

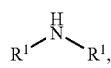 (I)

where
R$^1$ is alkyl, cycloalkyl, hydroxyalkyl, aminoalkyl, hydroxyalkylaminoalkyl, alkoxyalkyl, dialkylaminoalkyl, alkylaminoalkyl, aryl, heteroaryl, aralkyl, heteroarylalkyl, alkylaryl, alkylheteroaryl,
or $R^3R^4$N-A-, where A=$C_{1-6}$-alkylene or —$CH_2$—$CH_2$—O—($CH_2$—$CH_2$—O)$_n$—$CH_2$—$CH_2$— (where n=0, 1 or 2) and $R^3$, $R^4$=$C_{1-4}$-alkyl or together with the N-atom to which they are bound form a piperidine or morpholine ring,
or the two radicals $R^1$ together form —($CH_2$)$_l$—$CH_2$—X—($CH_2$)$_m$—, where
X is $CH_2$, CHR$^5$, oxygen (O), sulfur (S) or NR$^5$,
R$^5$ is hydrogen (H), alkyl, alkylphenyl,
l, m are each an integer from 1 to 4,
by reaction of a corresponding primary amine of the formula II or IIa

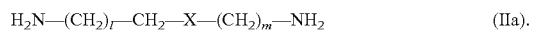

14. A process as claimed in claim 1 for preparing a symmetrical secondary amine of the formula I

where
R$^1$ is $C_{3-10}$-dialkylaminoalkyl, by reaction of a corresponding primary amine of the formula II

15. The process as claimed in claim 13, wherein
R$^1$ is $C_{1-200}$-alkyl, $C_{3-12}$-cycloalkyl, $C_{1-20}$-hydroxyalkyl, $C_{1-20}$-aminoalkyl, $C_{2-20}$-hydroxyalkylaminoalkyl, $C_{2-30}$-alkoxyalkyl, $C_{3-30}$-dialkylaminoalkyl, $C_{2-30}$-alkylaminoalkyl, aryl, heteroaryl, $C_{7-20}$-aralkyl, $C_{4-20}$-heteroarylalkyl, $C_{7-20}$-alkylaryl, $C_{4-20}$-alkylheteroaryl, or $R^3R^4$N-A-, where A=$C_{1-6}$-alkylene or —$CH_2$—$CH_2$—O—($CH_2$—$CH_2$—O)$_n$—$CH_2$—$CH_2$— (where n=0, 1 or 2) and $R^3$, $R^4$=$C_{1-4}$-alkyl or together with the N-atom to which they are bound form a piperidine or morpholine ring,
or the two radicals $R^1$ together form —($CH_2$)$_l$—$CH_2$—X—($CH_2$)$_m$—, where
X is $CH_2$, CHR$^5$, oxygen (O), sulfur (S) or NR$^5$,
R$^5$ is hydrogen (H), $C_{1-4}$-alkyl, $C_{7-40}$-alkylphenyl.

16. The process as claimed in claim 14, wherein R$^1$ is 3-(N,N-dimethylamino)propyl.

* * * * *